(12) United States Patent
Cosnier et al.

(10) Patent No.: US 7,947,836 B2
(45) Date of Patent: May 24, 2011

(54) BIOSENSOR AND METHOD OF DETECTION OF A DNA SEQUENCE

(75) Inventors: Serge A. Cosnier, Crolles (FR); Robert S. Marks, Omer (IL); Elena R. Ionescu, Bucharest (RO)

(73) Assignees: Universite Joseph Fourier - Grenoble 1 (FR); Ben-Gurion University of the Negev Research and Development Authority (IL); Centre National de la Recherche Scientifique - CNRS (FR)

( * ) Notice: Subject to any disclaimer, the term of this patent is extended or adjusted under 35 U.S.C. 154(b) by 794 days.

(21) Appl. No.: 11/824,799

(22) Filed: Jul. 2, 2007

(65) Prior Publication Data

US 2011/0068012 A1 Mar. 24, 2011

(51) Int. Cl.
*C07D 213/00* (2006.01)
*H01M 4/60* (2006.01)
*C12Q 1/68* (2006.01)
*G01N 15/06* (2006.01)

(52) U.S. Cl. .............. 546/1; 429/212; 429/215; 435/6; 422/68.1

(58) Field of Classification Search ...... 546/1; 429/212, 429/215; 435/6; 422/68.1
See application file for complete search history.

(56) References Cited

U.S. PATENT DOCUMENTS

2009/0314660 A1* 12/2009 Canonne et al. .............. 205/775

OTHER PUBLICATIONS

Giacomo Chiti et al., *Electrochemical DNA biosensor for environmental monitoring*, Analytica Chimica Acta, 2001, vol. 427, pp. 155-164, © 2001 Elsevier Science B.V.

J. Wang, *Electrochemical nucleic acid biosensors*, Analytica Chimica Acta, 2002, vol. 469, pp. 63-71, © 2002 Elsevier Science B.V.

J. Justin Gooding, *Electrochemical DNA Hybridization Biosensors*, Electroanalysis, 2002, vol. 14, No. 17, pp. 1149-1156, © 2002 Wiley-VCH Verlag GmbH & Co. KGaA, Weinheim.

T. G. Drummond et al., *Electrochemical DNA sensors*, Nature Biotechnology, Oct. 2003, vol. 21, No. 10, pp. 1192-1199, © 2007 INIST CNRS.

F. Patolsky et al., *Electronic Transduction of DNA Sensing Processes on Surfaces: Amplification of DNA Detection and Analysis of Single-Base Mismatches by Tagged Liposomes*, J. Am. Chem. Soc., 2001, vol. 123, pp. 5194-5205, © Am. Chem. Soc.

(Continued)

*Primary Examiner* — Jezia Riley
(74) *Attorney, Agent, or Firm* — DLA Piper LLP (US)

(57) ABSTRACT

The invention relates biosensor comprising a conductive or semi-conductive support and an intercalator polymer, wherein the intercalator polymer comprises monomer units of formula (I)

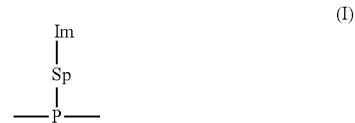

wherein P is an electropolymerizable moiety selected among the group consisting in pyrrole, acetylene, phenol, aniline, thiophene, carbazole and azulene; Sp is a spacer, and Im is an intercalator.

The invention also relates to a method for the detection of a DNA sequence with the biosensor, comprising the steps of:
- hybridizing the DNA sequence with a DNA probe for forming a dsDNA
- incubating the biosensor with the dsDNA for anchoring the dsDNA to the intercalator
- detecting the quantity of dsDNA on the biosensor.

12 Claims, 2 Drawing Sheets

OTHER PUBLICATIONS

J. Yang et al., *Detection of Chemically-Induced Damage in Layered DNA Films with Co(bpy)hd $3^{3+}$ by Square-Wave Voltammetry*, Electroanalysis, 2002, vol. 14, No. 21, pp. 1494-1500, © 2002 Wiley-VCH Verlag GmbH & Co. KGaA, Weinheim.

J. Wang et al., *Electrochemical Coding Technology for Simultaneous Detection of Multiple DNA Targets*, J. Am. Chem. Soc., 2003, vol. 125, pp. 3214-3215, © 2003 American Chemical Society.

J. Wang et al., *Ultrasensitive Electrical Biosensing of Proteins and DNA: Carbon-Nanotube Derived Amplification of the Recognition and Transduction Events*, J. Am. Chem. Soc., 2004, vol. 126, pp. 3010-3011, © 2004 American Chemical Society.

F. Davis et al., *Species differentiation by DNA-modified carbon electrodes using an ac impedimetric approach*, Biosensors and Bioelectronics, 2005, vol. 20, pp. 1531-1538, © 2004 Elsevier B.V.

H. Peng et al., *Electrochemical detection of DNA hybridization amplified by nanoparticles*, Biosensors & Bioelectronics, 2006, vol. 21, pp. 1727-1736, © 2005 Elsevier B.V.

L. Bouffier et al., *Reactivity of Pyrido [4,3,2-k/] acridines: Regioselective Formation of 6-Substituted Derivatives*, J. Org. Chem., 2004, vol. 69, No. 23, pp. 8144-8147, © 2004 American Chemical Society.

K. Shirato et al., *Detection of West Nile virus and Japanese encephalitis virus using real-time PCR with a probe common to both viruses*, Journal of Virological Methods, 2005, vol. 126, pp. 119-125, © 2005 Elsevier B.V.

H.E. Prince, PhD et al., *Assays for detecting West Nile Virus antibodies in human serum, plasma, and cerebrospinal fluid*, Clinical and Applied Immunology Reviews, 2005, vol. 5, pp. 45-63, © 2005 Elsevier Inc.

S.M. Gordon, MD et al., *West Nile fever: Lessons from the 2002 season*, Cleveland Clinic Journal of Medicine, May 2003, vol. 70, No. 5, pp. 449-454.

C. Huang et al., *First Isolation of West Nile virus from a Patient with Encephatlitis in the United States*, Emerging Infectious Diseases, Dec. 2002, vol. 8, No. 12, pp. 1367-1371, U.S.A.

F. Palmisano et al., *Correlation between Permselectivity and Chemical Structure of Overoxidized Polypyrrole Membranes Used in Electroproduced Enzyme Biosensors*, Analytical Chemistry, Jul. 1995, vol. 67, No. 13, pp. 2207-2211, © 1995 Am. Chem. Soc.

B. Wang et al., *New acridone derivatives for the electrochemical DNA-hybridisation labelling*, Bioelectrochemistry, 2004, vol. 63, pp. 233-237, © 2004 Elsevier B.V.

H. Korri-Youssoufi et al., *Electrochemical biosensing of DNA hybridization by ferrocenyl groups functionalized polypyrrole*, Analytica Chimica Acta, 2002, vol. 469, pp. 85-92, © 2002 Elsevier Science B.V.

S. Cosnier et al., *New flavin and deazaflavin oligonucleotide conjugates for the amperometric detection of DNA hybridization*, Chem. Commun., 2004, pp. 1624-1625, © The Royal Society of Chemistry 2004.

S. Hleli et al., *Impedance Spectroscopy Technique for DNA Hybridization*, Sensors, 2003, vol. 3, pp. 472-479, © 2003 by MDPI.

Y. Okahata et al., *Hybridization of Nucleic Acids Immobilized on a Quartz Cristal Microbalance*, J. Am. Chem. Soc., 1992, vol. 114, 8299-8300, © 1992 American Chemical Society.

Y. Ye et al., *DNA Electrochemical Behaviours, Recognition and Sensing by Combining with PCR Technique*, Sensors, 2003, vol. 3, pp. 128-145, © 2003 by MDPI.

J. Wang et al., *Indicator-free electrochemical DNA hybridization biosensor*, Analytica Chimica Acta, 1998, vol. 375, pp. 197-203, © 1998 Elsevier Science B.V.

D. Kambhampati et al., *Investigating the kinetics of DNA-DNA and PNA-DNA interactions using surface plasmon resonance-enhanced fluorescence spectroscopy*, Biosensors & Bioelectronics, 2001, vol. 16, pp. 1109-1118, © 2001 Elsevier Sci. B.V.

A.P. Abel et al., *Fiber-Optic Evanescent Wave Biosensor for the Detection of Oligonucleotides*, Anal. Chem., 1996, vol. 68, No. 17, pp. 2905-2912, © 1996 American Chemical Society.

R.C. Ebersole et al., *Spontaneously Formed Functionally Active Avidin Monolayers on Metal Surfaces:A Strategy for Immobilizing Biological Reagents and Design of Piezoelectric Biosensors*, J. Am. Chem. Soc., 1990, vol. 112, pp. 3239-3241, © 1995 Am. Chem. Soc.

J.L. McInnes et al., *Nonradioactive, photobiotin-labelled DNA probes for routine diagnosis of viroids in plant extracts*, Journal of Virological Methods, 1989, vol. 23, pp. 299-312, © 1989 Elsevier Science Publishers B.V.

G. Kejian et al., *Digoxigenin-Labeled Probes for the Detection of Hepatitis B Virus DNA in Serum*, Journal of Clinical Microbiology, Mar. 1991, vol. 29, No. 3, pp. 506-509, © 1991 American Society for Microbiology.

C.N. Campbell et al., *Enzyme-Amplified Amperometric Sandwich Test for RNA and DNA*, Anal. Chem., Jan. 2002, vol. 74, No. 1, pp. 158-162, © 2002 American Chemical Society.

T. de Lumley-Woodyear et al., *Direct Enzyme-Amplified Electrical Recognition of a 30-Base Model Oligonucleotide*, J. Am. Chem. Soc., 1996, vol. 118, No. 23, pp. 5504-5505, © 1996 American Chemical Society.

S-J. Park et al., *Array-Based Electrical Detection of DNA with Nanoparticle Probes*, Science, Feb. 2002, vol. 295, pp. 1503-1506, © 2002 The American Association for the Advancement of Science.

T. Ihara et al., *Gene sensor using ferrocenyl oligonucleotide*, Chem Commun., 1997, pp. 1609-1610.

C. Xu et al., *Electrochemical detection of sequence-specific DNA using a DNA probe labeled with aminoferrocene and chitosan modified electrode immobilized with ssDNA*, Anaylst, 2001, vol. 126, pp. 62-65, © 2001 The Royal Society of Chemistry.

E. Paleček et al., *From Polarography of DNA to Microanalysis with Nucleic Acid-Modified Electrodes*, Electroanalysis, 1996, vol. 8, No. 1, pp. 7-14, © 1996 VCH Verlagsgesellschaft mbH, D-69469 Weinheim.

K.M. Millan et al., *Sequence-Selective Biosensor for DNA Based on Electroactive Hybridization Indicators*, Anal. Chem., 1993, vol. 65, pp. 2317-2323, © 1993 American Chemical Society.

D.H. Johnston et al. *Electrochemical Measurement of the Solvent Accessibility of Nucleobases Using Electron Transfer between DNA and Metal Complexes*, J. Am. Chem. Soc., 1995, vol. 117, No. 35, pp. 8933-8938, © 1995 American Chemical Society.

E.L.S. Wong et al., *Electronic Detection of Target Nucleic Acids by a 2, 6-Disulfonic Acid Anthraquinone Intercalator*, Anal. Chem., Aug. 2003, vol. 75, No. 15, pp. 3845-3852, © 2003 American Chemical Society.

S. Takenaka et al., *DNA Sensing on a DNA Probe-Modified Electrode Using Ferrocenylnaphthalene Diimide as the Electrochemically Active Ligand*, Anal. Chem., Mar. 2000, vol. 72, No. 6, pp. 1334-1341, © 2000 American Chemical Society.

P.B. Dervan et al., *Sequence-specific DNA recognition by polyamides*, Biopolymers, Chemical Biology, 1999, vol. 3, pp. 688-693, © 1999 Elsevier Science Ltd.

D.E. Wemmer, *Ligands Recognizing the Minor Groove of DNA: Development and Applications*, Biopolymers (Nucleic Acid Sciences), 1999/2000, vol. 52, p. 197-211, © 2001 John Wiley & Sons, Inc.

J.G. Pelton et al., *Structural Characterization of a 2:1 Distamycin A·d(CGCAAATTGGE) Complex by Two-Dimensional NMR*, Biochemistry, Proc. Natl. Acad. Sci. U.S.A., Aug. 1989, vol. 86, pp. 5723-5727.

J.G. Pelton et al. *Structural Modeling of the Distamycin A-d(CGCGAATTCGCG)HD 2 Complex Using 2D NMR and Molecular Mechanics*, Biochemistry, 1988, vol. 27, No. 21, pp. 8088-8096, © 1988 American Chemical Society.

J.M. Gottesfeld et al., *Sequence-specific Recognition of DNA in the Nucleosome by Pyrrole-Imidazole Polyamides*, J. Mol. Biol., 2001, vol. 309, pp. 615-629, © 2001 Academic Press.

M.D. Frank-Kamenetskii et al., *Triplex DNA Structures*, Annu. Rev. Biochem., 1995, vol. 64, pp. 65-95, © 1995 Annual Reviews Inc.

S. Diviacco et al., *Site-directed inhibition of DNA replication by triple helix formation*, The FASEB Journal, Dec. 2001, vol. 15, pp. 2660-2668, © FASEB.

J. Wang et al., *Screen-Printed Electrochemical Hybridization Biosensor for the Detection of DNA Sequences from the Escherichia Coli Pathogen*, Electroanalysis, 1997, vol. 9, No. 5, pp. 395-398, © VCH Verlagsgesellschaft mbH, D69469 Weinheim.

P.M. Armistead et al. *Modification of Indium Tin Oxide Electrodes with Nucleic Acids: Detection of Attomole Quantities of Immobilized DNA by Electrocatalysis*, Anal. Chem., August 2000, vol. 72, No. 16, pp. 3764-3770, © 2000 American Chemical Society.

S.K. Arora, *Molecular Structure, Absolute Stereochemistry, and Interactions of Nogalamycin, a DNA-Binding Anthracycline Antitumor Antibiotic*, J. Am. Chem. Soc., 1983, vol. 105, No. 5, pp. 1328-1332, © 1983 American Chemical Society.

M. Takagi, *Threading intercalation to double-stranded DNA and the application to DNA sensing. Electrochemical array technique*, Pure Appl. Chem., 2001, vol. 73, No. 10, pp. 1573-1577, © 2001 IUPAC.

S.O. Kelly et al., *Electrochemistry of Methylene Blue Bound to a DNA-Modified Electrode*, Bioconjugate Chem., 1997, vol. 8, No. 1, pp. 31-37, © 1997 American Chemical Society.

K. Hashimoto et al., *Sequence-Specific Gene Detection with a Gold Electrode Modified with DNA Probes and an Electrochemically Active Dye*, Anal. Chem., November 1994, vol. 66, No. 21, pp. 3830-3833, © 1994 American Chemical Society.

M.T. Carter et al. *Voltammetric Studies of the Interaction of Metal Chelates with DNA. 2. Tris-Chelated Complexes of Cobalt (III) and Iron (II) with 1,10-Phenanthroline and 2, 2'-Bipyridine*, J. Am. Chem. Soc., 1989, vol. 111, pp. 8901-8911 © 1989 Am. Chem. Soc.

S. Cosnier et al., *Electroenzymatic Polypyrrole-intercalator Sensor for the Determination of West Nile Virus cDNA*, Anal. Chem., October 2006, vol. 78, No. 19, pp. 7054-7057, © 2006 American Chemical Society.

* cited by examiner

BIOSENSOR AND METHOD OF DETECTION OF A DNA SEQUENCE

The instant application contains a Sequence Listing which has been submitted in ASCII format via EFS-Web and is hereby incorporated by reference in its entirety. Said ASCII copy, created on Dec. 16, 2010, is named REG07208.txt and is 791 bytes in size.

The present invention relates to a biosensor for detecting a DNA sequence and a method of detection of a DNA sequence, using intercalators.

BACKGROUND OF THE INVENTION

Nowadays, there is a tremendous interest in the development of portable, easy-to-use and low cost bioanalytical systems for the rapid diagnosis of genetic or infectious diseases. DNA hybridization biosensors have become one of such major diagnostic tools. Mostly, signal transduction of the hybridization event is based on optical, electrochemical, and microgravimetrical DNA methods. The electrochemical DNA biosensor holds, among all these, great promise due to a simple, rapid and inexpensive approach (1-4). Moreover, electrochemical DNA sensors could have the lower detection limit in the femtomolar or attomolar range, that usually is lower than the detection limit of general analytical techniques such as gel electrophoresis or membrane blots, which in addition are too slow and labour intensive.

Usually, electrochemical DNA hybridization biosensor is based on a one strand DNA (ssDNA) probe connected to a physical transducer whose properties are modified upon hybridization with the complementary DNA target to the probe. The goal of the sensor is to convert the DNA hybridization into an analytical signal measurable.

The DNA electrochemical sensors rely on the immobilization of a ssDNA or oligonucleotides onto the electrode surface to recognize through base pairing the complementary DNA strand (target) or oligonucleotides in a sample solution. The distribution, packing density and orientation of the attached probe may affect the performance of DNA biosensors.

Because of its importance, in literature there are several articles reviewing the design of DNA biosensors with aspect to transducer surface and probe immobilization towards sensitive hybridization detection. Thus, immobilization methods vary depending on the kind of transducer surface (gold, platinum, silver, indium tin oxide, etc.) and the application. Some of the most representative immobilization techniques are covalent attachment on a functionalized surface, adsorption on surface, embedding in sol-gel or polymeric matrix, affinity immobilization and self-assemble monolayer method (22).

Over the years, different forms of electrochemical DNA biosensors have been developed which transduce the DNA hybridization process using either a redox active molecule or a label free method which relies on the intrinsic redox-active properties of DNA base or a change of the electrical properties of the electrode interface upon hybridization, respectively (5-10, 23-34).

However, all known biosensors require the functionalization of their surface with specific ssDNA or oligonucleotides prior to the measurement. These biosensors are thus immersed into a solution containing a mixture with a ssDNAs and only the ssDNA target hybridizes onto the complementary ssDNA probe immobilized on the sensor.

Besides, such biosensors cannot be reused because they are modified by a specific oligonucleotide sequence.

Furthermore, all the DNA ligands as classical intercalators—like methylene blue—, groove binders and metal chelates are generally suffering from the impossibility of discriminating the double-stranded from the single-stranded DNAs, poor electrochemical performances in terms of reversibility, overpotential and/or stability.

One goal of the invention is therefore to avoid these drawbacks and to define an intercalator polymer that allows a better discrimination of dsDNA from ssDNA. Another goal of the invention is to define a new biosensor that does not need to be pre-modified with a specific DNA sequence probe. Another goal of the invention is to provide a biosensor that could be reused. Another goal of the invention is to define a method of detection of a DNA sequence that can discriminate better dsDNA from ssDNA.

BRIEF DESCRIPTION OF THE INVENTION

The present invention concerns an intercalator polymer comprising monomer units of the following formula:

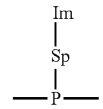

wherein P is an electropolymerizable moiety selected among the group consisting in pyrrole, acetylene, phenol, aniline, thiophene, carbazole and azulene; Sp is a spacer and Im is an intercalator.

The intercalator polymer according to the invention advantageously comprises monomer units of the following formulas:

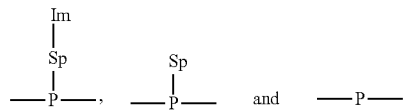

wherein P, Sp and Im are defined above.

In preferred embodiments, the molar ratio Im/P is comprised between 1/10 and 1/5.

In a preferred embodiment, P is a pyrrole.

The spacer Sp is selected to allow grafting of a sufficient amount of intercalator Im on the polymer backbone. It may be selected among alkylenyl groups, cycloalkylenyl groups, alkenylenyl groups. The spacer Sp may be substituted by one or more substituents.

According to the present invention, the spacer moiety Sp comprises between 3 and 15 atoms. Particularly, for the spacer Sp according the invention, alkenyl groups are preferably C3-C15 linear or branched alkenyl groups, including methylenyl, ethylenyl, propylenyl, butylenyl, pentylenyl and hexylenyl radicals. The same definition applies for the alkenylenyl groups, but where it comprises one or more unsaturated bonds.

Cycloalkenyl groups are preferably C3-C6 cycloalkylenyl groups, including cyclopropylenyl, cyclopentylenyl and cyclohexylenyl groups.

One or more —$CH_2$— or —CH< groups of the spacer may be replaced by an oxygen, an amino or a carbonyl group.

The intercalator Im may be linked to the spacer through an appropriate covalent bond, more particularly a —COO—N— bond.

In a preferred embodiment of the invention, the spacer Sp is a radical of the following formula

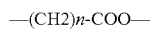  (IV)

wherein n is an integer ranging from 2 to 4, preferably 3.

The intercalator Im is preferably selected among the group consisting of metal polypyridine complexes, organic dyes such as methylene blue, compounds containing polycyclic aromatic rings such as naphthalene and phenanthroline derivatives, anthracyline antibiotics such as daunomycin, trypanocides, acridines and flavin and proflavin derivatives.

A preferred intercalator Im is a redox acridone derivate of the following formula:

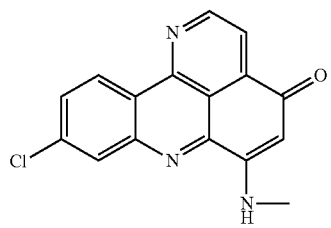

The present invention also concerns a redox acridone derivate (RAD) intercalator polypyrrole comprising monomers of the following formula:

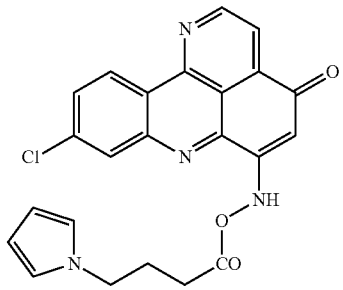

In preferred embodiments, the molar ratio RAD/pyrrole is comprised between 1/10 and 1/5.

The present invention also concerns a biosensor comprising a conductive or semi-conductive support and an intercalator polymer, wherein the intercalator polymer comprises monomer units of the following formula:

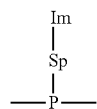

wherein P is an electropolymerizable moiety selected among the group consisting in pyrrole, acetylene, phenol, aniline, thiophene, carbazole and azulene; Sp is a spacer and Im is an intercalator.

In preferred embodiments, the biosensor according to the invention comprises monomer units of the following formulas:

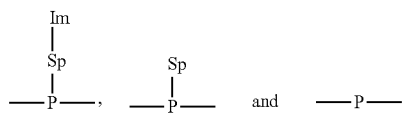

The molar ratio Im/P is advantageously comprised between 1/10 and 1/5.

In preferred embodiments, P is a pyrrole.

The spacer Sp is advantageously selected among alkylenyl groups, cycloalkylenyl groups, alkenylenyl groups, eventually substituted by one or more substituents.

The intercalator Im is preferably selected among the group consisting of metal polypyridine complexes, organic dyes such as methylene blue, compounds containing polycyclic aromatic rings such as naphthalene and phenanthroline derivatives, anthracyline antibiotics such as daunomycin, trypanocides, acridines and flavin and proflavin derivatives.

In preferred embodiments, the intercalator Im is a redox acridone derivate of the following formula:

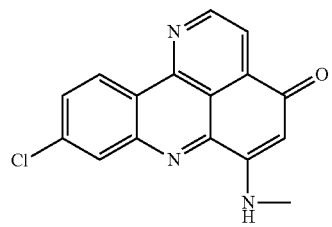

In preferred embodiments of the biosensor according to the invention, the intercalator polymer is coated on the conductive or semi-conductive support. Such conductive or semi-conductive support may be selected among metallic supports such as platinum, gold, $TiO_2$, Indium Tin oxide or carbon materials such as glassy carbon, graphite, carbon paste, screen printed carbon.

The conductive or semi-conductive support may be an electrode. Such an electrode may preferably consist in a platinum disk having a diameter of about 0.5 cm.

The present invention also concerns a method for the preparation of a biosensor comprising on a conductive or semi-conductive support an intercalator polymer comprising monomer units of the following formula:

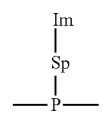

wherein P is an electropolymerizable moiety selected among the group consisting in pyrrole, acetylene, phenol, aniline, thiophene, carbazole and azulene; Sp is a spacer and Im is an intercalator, the method comprising the steps of:

electropolymerizing onto the conductive or semi-conductive support a polymerizable moiety of the following formula:

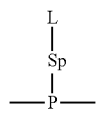

wherein L is a leaving group, and grafting an intercalator Im on one or more spacers of the polymer.

The leaving group L is advantageously selected among the group consisting in N-hydroxy succinimide (NHS), N-hydroxy phthalimide (NHP) or pentafluorophenol carboxylate group. In a preferred embodiment, the leaving group L is a group of the following formula:

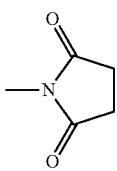

The polymerizable moiety is a moiety of the following formula:

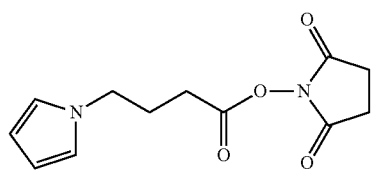

In preferred embodiments, the molar ratio Im/P is comprised between 1/10 and 1/5.

The present invention also concerns a method for the detection of a DNA sequence with a biosensor comprising a conductive or semi-conductive support and an intercalator polymer, wherein the intercalator polymer comprises monomer units of the following formula:

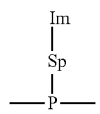

wherein: P is an electropolymerizable moiety selected among the group consisting in pyrrole, acetylene, phenol, aniline, thiopohene, carbazole and azulene; Sp is a spacer, and Im is an intercalator, the method comprising the steps of:
  hybridizing the DNA sequence with a DNA probe for forming a dsDNA
  incubating the biosensor with the dsDNA for anchoring the dsDNA to the intercalator
  detecting the quantity of dsDNA on the biosensor.

In preferred embodiments, the intercalator polymer comprises monomer units of the following formulas:

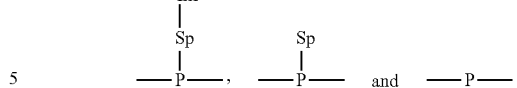

wherein P, Sp and Im are below.

The molar ratio Im/P is comprised between 1/10 and 1/5.
In preferred embodiments, P is a pyrrole.
The spacer Sp is advantageously selected among alkylenyl groups, cycloalkylenyl groups, alkenylenyl groups, eventually substituted by one or more substituents.

The intercalator Im may be selected among the group consisting of metal polypyridine complexes, organic dyes such as methylene blue, compounds containing polycyclic aromatic rings such as naphthalene and phenanthroline derivatives, anthracyline antibiotics such as daunomycin, trypanocides, acridines and flavin and proflavin derivatives. In a preferred embodiment, the intercalator Im is a redox acridone derivate of the following formula:

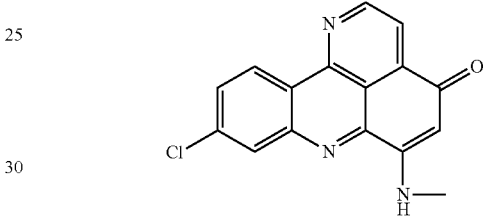

The intercalator polymer is coated on the conductive or semi-conductive support. Such conductive or semi-conductive support may be selected among metallic supports such as platinum, gold, $TiO_2$, Indium Tin oxide or carbon materials such as glassy carbon, graphite, carbon paste, screen printed carbon.

The conductive or semi-conductive support may be an electrode.

In preferred embodiments of the method according to the invention, the hybridization step is performed at a temperature comprised between 5 and 50° C., during 1 min to 10 h.

The detection step may be carried out by cyclic voltammetry, by the measurement of the frequency changes of a quartz crystal microbalance, or, if the DNA probe is biotin-labeled, by amperometry.

The invention also concerns a device for the detection of a DNA sequence in a sample, comprising:
  a plurality of wells containing a solution comprising the sample and a DNA probe, and
  a plurality of biosensors adapted for being immersed into the wells for allowing the anchoring of the dsDNA onto the biosensors,
wherein the biosensors comprise a conductive or semi-conductive support and an intercalator polymer, wherein the intercalator polymer comprises monomer units of the following formula:

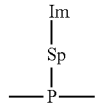

wherein P is an electropolymerizable moiety selected among the group consisting in pyrrole, acetylene, phenol, aniline, thiophene, carbazole and azulene; Sp is a spacer, and Im is an intercalator.

In preferred embodiments of the device according to the invention, the number of wells is at least 10; it can be around 100 and possibly till 10 000, and the area of the opening of the wells is at least $2.5\ 10^{-3}\ mm^2$, and possibly till $1\ cm^2$.

BRIEF DESCRIPTION OF THE FIGURES

FIG. 2A represents the polypyrrole electroactivity and FIG. 2B represents the polypyrrole overoxidation.

DETAILED DESCRIPTION OF THE INVENTION

General Principle of the Invention

Figure 1A:
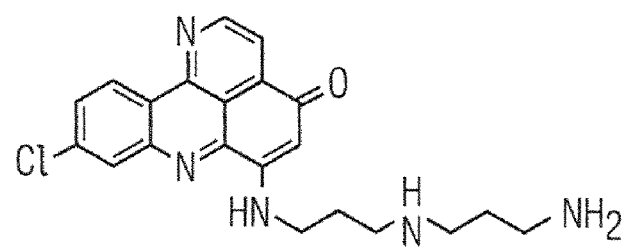
FIG. 1A shows the structure of the redox acridone derivate (RAD)

The original method of detection of a DNA sequence according to the invention comprises the following steps.

The first step is the preparation of a biosensor, comprising forming by electropolymerization an, intercalator polymer film onto a conductive or semi-conductive support. The covalent bonding between the polymer and an intercalator is made either prior or after polymerization, preferably after polymerization.

Methods for electropolymerization of polymers according to the invention are well known in the art and extensively disclosed in the scientific literature (see cited publications).

The next step is the hybridization of the ssDNA target with a ssDNA probe in a mixture to form dsDNA.

Methods for hybridization of ssDNA with a probe are also well known in the art and extensively disclosed in scientific literature and other handbooks.

The next step is the incubation of the biosensor in the mixture in order to allow the capture of the dsDNA by the intercalator.

Then, a method of detection can be used in order to detect quantitatively or qualitatively the presence of dsDNA on the biosensor.

All direct or indirect detection methods known by one skilled in the art can be used. Examples of use of cyclic voltammetry and amperometry will be described in detail in the experimental section below. It is also possible to use a label-free method relying on electrochemical impedance spectra (EIS) for monitoring the interfacial property changes of modified electrodes upon hybridization event (20). A method based on the measurement of the frequency changes of a quartz crystal microbalance (QCM) can also be implemented (21).

A device for the detection of a DNA sequence in a sample can be elaborated. The device comprises a plurality of wells, each well containing a solution comprising the sample and a determined ssDNA probe. Hybridization occurs in the well(s) in which the ssDNA probe is complementary to the DNA sequence of the sample, thus forming a dsDNA.

The device also comprises a plurality of biosensors adapted for being immersed into the wells. According to a preferred embodiment, all the biosensors are fabricated by the method described above, on a single conductive support having as many spots as the number of wells. All the spots are formed on the conductive electrode by electropolymerization of an intercalator polymer.

The spots are immersed into the corresponding wells and, if the wells contain dsDNA, the dsDNA is grafted to the intercalator of the corresponding biosensor(s).

After detection, the support can then be washed into an acid or basic bath, which eliminates the dsDNA, whereas the polymer, which is stable, remains. The support can therefore be re-used.

The use of intercalators is widespread for the labelling after hybridization of DNA probe and DNA target and therefore their detection and quantification are well known (35-52). This represents a large family of compounds that have already been tested for the detection step.

In fact, the present invention is applicable to all intercalators produced until now for insertion into the double DNA helix.

Furthermore, this strategy of detection of a single stranded DNA by hybridization in a solution with its complementary followed by the anchoring of the resulting double stranded DNA by an intercalator, is applicable to every kind of sensor used for the detection of biomolecules (electrodes, optical fibers, field effect transistors, etc.).

This new concept of DNA detection may also bring an increased sensitivity and more precisely an increased limit of detection for the direct detection methods. Indeed, the classical direct detection of duplex formed on the surface on sensor that has been pre-functionalized by a ssDNA—for example, impedance or gravimetric measurements—is based on a perturbation linked to the difference (transfer resistance, weight, etc) between a single stranded and a double stranded DNA.

In the grafted intercalator concept, the difference will be noticeably more important because it will concern a small molecule (the intercalator) and a dsDNA; a better detection sensitivity is therefore expected.

Another interesting advantage is the possibility to re-use the biosensor for several measurements of the same target, by a simple denaturation of the duplex. A specific advantage of this method compared to the other DNA sensors is the possibility to re-use the sensor for other targets. Indeed, the recognition specificity lies into the formation of the dsDNA, the anchoring step being only specific of the duplex. This is an important point when expensive biosensors are used.

At last, another advantage of the invention is that the functionalization of the surface of the sensor is very simple compared to grafting DNA probes onto the surface.

Experimental Section

The approach was based on the covalent attachment of a synthetic planar intercalator, a redox acridone intercalator (RAD) onto an electropolymerized polypyrrole film functionalized by activated esters groups. One example is a redox acridone derivate (RAD) recently synthesized (11) that was used for the successfully determination of ssDNA derived from West Nile Virus sequence (ssDNA-WNV).

For this purpose, the complementary DNA strand (target) mixed into an aqueous solution with the DNA probe were captured and thus, immobilized directly on the electrode surface via RAD-duplex intercalation, RAD being anchored onto a new electropolymerized polypyrrole N-hydroxysuccinimide film.

The WNV Virus

Because of the rising epidemy of WNV infections with no good antivirals or vaccines in sight, a greater reliance on early WNV diagnostics is needed (12). First isolated in Uganda in 1937, WNV is a single-stranded RNA flavivirus transmitted to humans by an infected mosquito bite and is constituted of three structural proteins (C, prM, E). The envelope protein (E protein) is arranged in dimers on the surface of the mature virions and is one of the preferential targets for the diagnosis of WNV infection by RT-PCR or ELISA due to its high immunogenity. Human-to-human transmission via mosquito bites does not occur; however, WNV can be transmitted from one person to another via blood transfusion, organ transplantation, breast-feeding, and transfer across the placenta (13).

Although most WNV infected persons are asymptomatic, 10-20% develop symptoms such as fever, headache, rash, and malaise. A small number (<1%) of infected individuals develop severe neurological illness, including meningitis, encephalitis, and acute flaccid paralysis; the infection proves to be fatal for 10% of these patients with neurological illness (14).

The elaboration of a new concept of DNA sensor based on the revolutionary use of an intercalator molecule as a mechanical vector to extract a double stranded DNA from an aqueous solution by its deposition on the transducer surface is reported here. In this context, a WNV genomic sensor was selected as a model. The target sequence is derived from a primer sequence used in RT-PCR and previously tested and published by Huang et al. (15).

The detailed steps in the elaboration of WNV-ssDNA sensor are described below.

Immobilization of the RAD on the Sensor Surface

A pyrrole-NHS monomer was synthesized as follows: 4-pyrrol-1-ylbutanoic acid (298 mg, 1.9 mmol), N-hydroxysuccinimide (228 mg, 2.0 mmol), and 1,3-dicyclohexylcarbodiimide (398 mg, 2.0 mmol) were dissolved in dry tetrahydrofuran. The mixture was stirred under argon overnight at room temperature and then filtered. The organic phase was evaporated, and the residue was washed with $CH_2Cl_2$. Crystallization from $CH_2Cl_2$ gave 494 mg of monomer pyrrole-NHS (60% yield). $^1H$ NMR (250 MHz/$CDCl_3$): δ (ppm) 6.62 (s, 2H), 6.09 (s, 2H), 3.83 (t, 2H), 2.80 (s, 4H), 2.54 (t, 2H), 1.92 (m, 2H). PBS buffer was 0.1 M phosphaten buffer (pH 7) containing 0.145 M NaCl.

Figure 1B:
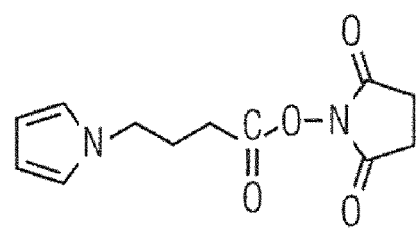
FIG. 1B shows the structure of the pyrrole N-substituted by N-hydroxysuccinimide group (pyrrole-NHS)

To immobilize the intercalator on the Pt disk electrode (5 mm-diameter), a new pyrrole derivative functionalized with a N-hydroxysuccinimide group (pyrrole-NHS) (represented on FIG. 1B) was prepared by reaction of 4-pyrrolylbutanoic acid with N-hydroxysuccinimide and characterized by NMR technique. Electropolymerization of pyrrole-NHS (5 mM) in solution of $CH_3CN+0.1$ M $LiClO_4$ was accomplished by controlled potential oxidation (2 mC) at 0.95V.

Figures 2A, 2B:
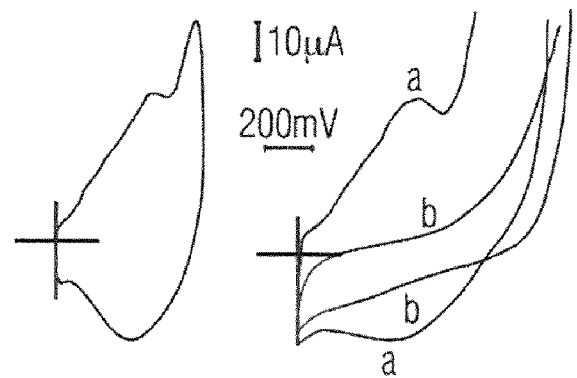
FIGS. 2A and 2B are the cyclic voltammograms of poly (pyrrole-NHS) electrode (diameter 5 mm)

Upon transfer into $CH_3CN+0.1$ M $LiClO_4$ solution free of monomer, the cyclic voltammogram of the resulting electrode exhibits a reversible peak system at 0.45 V (shown on FIG. 2A). The latter corresponds to the oxidation of the polypyrrolic film formed on the electrode surface. The apparent surface coverage ($\Gamma'=1.55\times10^{-8}$ mol·cm$^{-2}$) of electropolymerized pyrol-NHS was determined from the charge recorded under polypyrrole electroactivity, the electrochemical polymerization yield being 35%.

Referring now to FIG. 2B, to increase the polymer permeability, an overoxidation of the polypyrrole film was performed by cycling the potential between 0.0 and 1.3 V. On this figure, (a) corresponds to the first scan whereas (b) corresponds to the fourth scan in $CH_3CN+0.1$ M $LiClO_4$; the scan rate being 0.1 V·s$^{-1}$.

Further, the covalent binding of the RAD intercalator was carried out at room temperature, by spreading over the modified electrode an aqueous RAD solution (20 μL, 140 μg/mL) for an overnight incubation under a wet environment. The structure of the RAD is shown on FIG. 1A.

Recognition (Hybridization) of the ssDNA Target Derived from a West Nile Virus Sequence and ssDNA Probe Hybridization between the denatured biotinylated oligonucleotide probe (140 μg/mL, 65° C. for 1 min) and various WNV-DNA target concentrations (1 pg to 100 μg/mL, 95° C. for 1 min) were performed in "a tube" for 1 h, at room temperature. The volume of the hybridization mixture was 0.2 mL. DNA hybridization buffer was based on 0.2 M phosphate buffer (pH 7) containing 12.5 mM PEG 8000, 0.5 M NaCl, 0.5 mM EDTA and 0.5% (w/v) SDS. Denatured salmon sperm solution 1% (v/v) (95° C. for 1 min) was added in the hybridization buffer. All buffers were sterilized by autoclaving for 30 min at 120° C. In house sterilized and deionized water was used in all solutions. The WNV oligonucleotides were provided by Integrated DNA Technologies having the following sequences:

target-DNA: GCTATTTGGCTACCGTCAGCATCTCTC-CACCAAAG-3', (+) (SEQ ID NO: 1);
WNV-DNA-biotin: 5'-CGGTAGCCAAATAGC/biotin/-3', (−) (SEQ ID NO: 2).

Capture of the Formed dsDNA by the Sensor Intercalator

To investigate the anchoring properties of the RAD into dsDNA, a WNV-derived DNA target was mixed with the biotinylated complementary oligonucleotide and the modified electrode was incubated with the hybridization solution for 2 h at 25° C. The modified electrodes were washed successively with 30 mM citrate buffer (pH 7) containing 0.3 M NaCl and 1% (w/v) SDS, then with 15 mM citrate buffer+150 mM NaCl+1% (w/v) SDS, then with 15 mM citrate buffer+150 mM NaCl, and finally with 10 mM PBS containing 0.5% SDS.

After incubation with the dsDNA, the poly(pyrrole-NHS)-RAD electrodes were treated for 30 min with 20 μL of a blocking solution, a PBS buffer (pH 7) containing 10 g·L$^{-1}$ BSA and 0.05% (v/v) Tween 20. The resulting electrodes were then incubated for another 20 min with 20 μL of avidin (500 μg/mL) and washed with PBS (pH 7) containing 0.5% (w/v) SDS. Finally, the modified electrodes were treated with 20 μL of biotinylated glucose oxidase (GOX) solution (500 μg/mL) for 20 min and rinsed with PBS (pH7) containing 0.5% (w/v) SDS.

Direct DNA Detection by Cyclic Voltammetry

The electrochemical behavior of modified dsDNA-RAD-poly(pyrrole-NHS) electrodes was examined by cyclic voltammetry in deaerated PBS (pH 7) buffer.

Figure 2C:
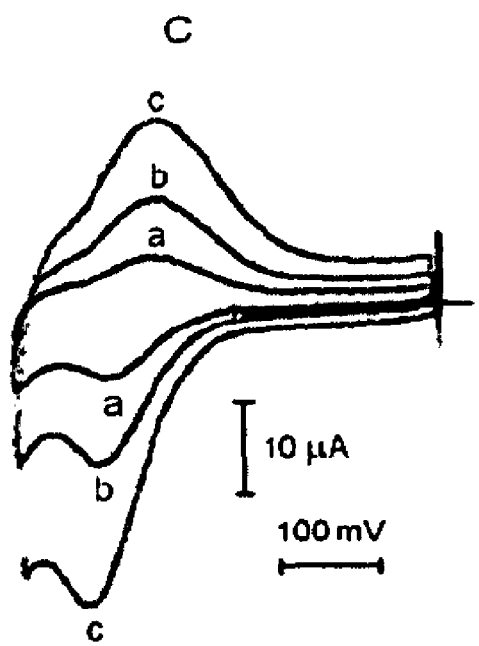
FIG. 2C shows the cyclic voltammograms of a poly(pyrrole-NHS) after the chemical grafting of RAD in deaerated PBS.

FIG. 2C shows a reversible peak system at −0.35V whereas the poly(pyrrole-NHS) film is not electroactive in this potential range. On this figure, the curves (a), (b) and (c) correspond respectively to scan rates 20, 50 and 100 mV·s$^{-1}$.

This redox signal is in good accordance with the potential value (−0.25 V) recorded for the one-electron reduction of RAD in solution.

In addition, the current intensity of this peak system varies linearly with the scan rate, corroborating thus the chemical grafting of RAD. The apparent surface coverage of RAD, $2.25\times10^{-9}$ mol·cm$^{-2}$, was estimated by integration of the charge under this peak system. Taking into account that the theoretical maximum surface coverage with one close-packed RAD layer corresponds to $2.37\times10^{-10}$ mol·cm$^{-2}$, it clearly appears that the intercalator molecules are grafted at the polymer-solution interface but also inside the polypyrrole structure.

Figure 2D:
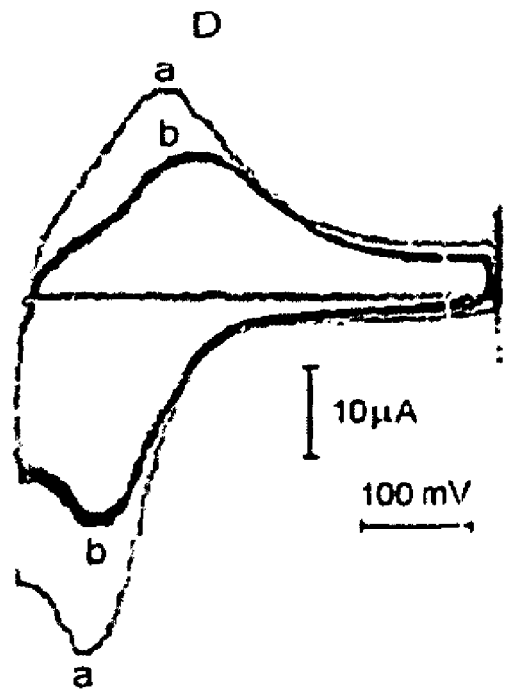
FIG. 2D shows the cyclic voltammograms of a poly(pyrrole-NHS) before and after incubation with WNV dsDNA.

As shown on FIG. 2D, that shows cyclic voltammograms before (a) and after (b) incubation with WNV dsDNA (10 ng/ml) in PBS, the scan rate being 0.1 V·s$^{-1}$, the dsDNA-incubation step clearly induces a decrease in current intensity of the reversible peak system at −0.35 V that was ascribed to the intercalation of the grafted RAD into the formed WNV-DNA duplex. Indeed, the disappearance of the electrochemical signal of similar acridone derivatives in solution in the presence of dsDNA was recently described and attributed to an intercalation process (17).

In contrast, no peak evolution was observed on the cyclic voltammogram of a similar electrode before and after its incubation in PBS solution containing only the WNV-DNA target (0.1 mg/mL) and noncomplementary oligonucleotide.

Such decrease may be attributed to a reduced insertion rate of counterions into the film during the electroreduction of RAD due to the steric hindrances, electrostatic repulsion, or both resulting from the duplex attachment at the polymer surface (18). As previously reported for oligonucleotides functionalized by redox groups (19), the intercalative binding of RAD to dsDNA and its strong interaction with the "π-stack" of the DNA base pairs diminish its accessibility and hence may also prevent its electrochemical reduction by an electron hopping process. Moreover, dsDNA anchored onto RAD-polypyrrolic film is stable since no evolution of the electrochemical signal was recorded after one-day storage in PBS.

However, the electroactivity of covalently bound RAD was not totally suppressed by the specific anchoring of hybridized WNV DNA since the bulky duplex cannot penetrate inside the polymer film. As a consequence, the decrease in current intensity of the RAD system cannot constitute an extremely sensitive method to quantify hybridization process.

Indirect DNA detection by amperometry using labelled ssDNA probe with biotin

Since the DNA-probe was biotin labeled, the presence of the WNV duplex was electroenzymatically detected by the attachment of a biotinylated enzyme onto the duplex via avidin-biotin affinity interactions. For this purpose, the poly(pyrrole-NHS)-RAD electrodes were incubated with duplex solutions formed from DNA target concentrations ranging from 1 pg up to 100 µg/mL. After the "fishing step", a biotinylated GOX was fixed by an avidin bridge onto the immobilized dsDNA. Since GOX catalyzes the aerobic oxidation of glucose with the concomitant production of $H_2O_2$, its presence was detected via the electrochemical oxidation of $H_2O_2$ at the underlying electrode surface potentiostated at 0.6 V.

Figure 3:
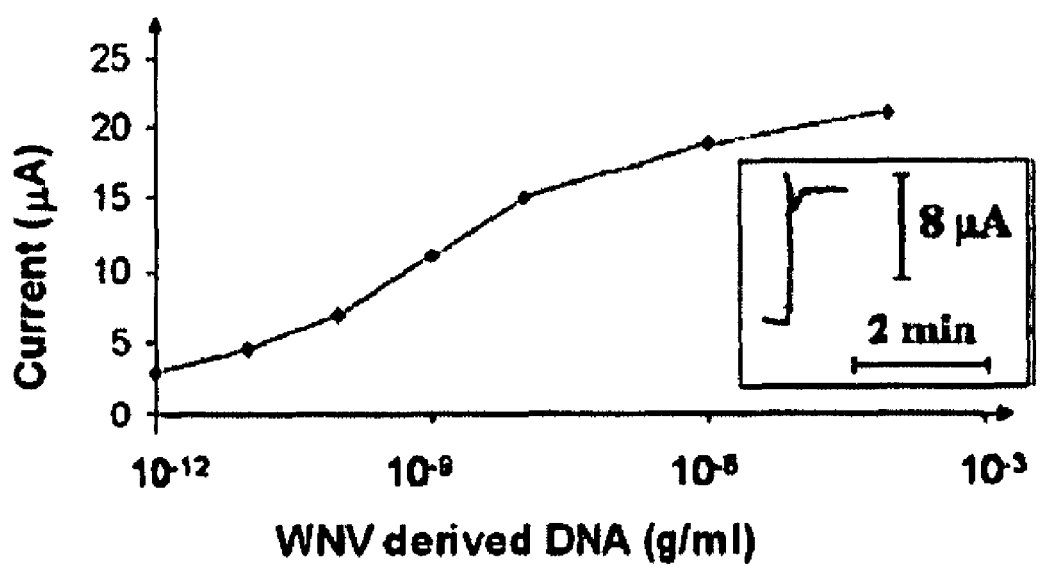
FIG. 3 is the amperometric current response of the poly (pyrrole-NHS)-RADdsDNA sensors as a function of DNA target concentration.

The current response of the poly(pyrrole-NHS)-RAD-dsDNA electrodes toward glucose (20 mM) was assayed in PBS (pH 7). The results are shown on FIG. 3 where the inset presents the current response of a DNA electrode to glucose (20 mM) for 1 ng/mL DNA target and E=0.6 V/Ag/AgCl. The current response reached a steady-state value in a very short time (30-40 s). These current responses were proportional to the DNA target concentration, the detection limit being 1 pg/mL (90 fM). The repeatability and reproducibility of the current response of the poly(pyrrole-NHS)-RAD-dsDNA electrodes were examined. For each DNA target concentration, three measurements of 20 mM glucose were carried out leading to relative standard deviation (RSD) values ranging from 1.7 to 2.0%. The elaboration of the DNA sensor was also reproducible; four poly(pyrrole-NHS)-RAD-dsDNA electrodes were prepared from 1 ng/mL DNA target and their amperometric responses led to a RSD of 3.7%.

Control Experiments of the WNV DNA Sensor Specificity

To ensure that the amperometric detections are directly related to the DNA hybridization phenomenon of various WNV-cDNA target concentrations, the intercalator (RAD) was replaced by glycine in the construction of the DNA sensor. Another control experiment consisted in the incubation of the poly(pyrrole-NHS)-RAD electrode with biotinylated ssDNA probe instead of dsDNA. Both controls were treated for GOX anchoring, and their amperometric responses to glucose were recorded. It clearly appears that these responses were very low (~100 nA) compared to the current response characteristic to 1 pg/mL DNA target concentration (3 µA).

CONCLUSION

These results demonstrate that an electrochemical WNV genomic sensor, using a DNA intercalator, can be extremely sensitive and could be adapted to detect an early stage of a WNV infection.

REFERENCES (1) Chiti, G.; Marrazza, G.; Mascini, M., Anal. Chim. Acta 2001, 427, 155-164
(2) Wang, J., Anal. Chim. Acta 2002, 469, 63-71
(3) Gooding, J. J., Electroanalysis 2002, 14, 1149-1156
(4) Drummond, T. G.; Hill, M. G.; Barton, J. K., Nat. Biotechnol. 2003, 21, 1192-1199
(5) Patolsky, F.; Lichtenstein, A.; Willner, I., J. Am. Chem. Soc. 2001, 123, 5194-5205
(6) Yang, J.; Zhang, Z.; Rusling, J. F., Electroanalysis 2002, 14, 1494-1500
(7) Wang, J.; Liu, G.; Merkoci, A., J. Am. Chem. Soc. 2003, 125, 3214-3215
(8) Wang, J.; Liu, G.; Jan, M. R., J. Am. Chem. Soc. 2004, 126, 3010-3011
(9) Davis, F.; Nabok, A. V.; Higson, S. P., Biosens Bioelectron. 2005, 20, 1531-1538
(10) Peng, H.; Soeller, C.; Cannell, M. B.; Bowmaker, G. A.; Cooney, R. P.; Travas-Sejdic, J., Biosens Bioelectron. 2006, 21, 1727-1736
(11) Bouffier, L.; Demeunynck, M.; Milet, A.; Dumy, P., J Org. Chem. 2004, 69, 8144-8147
(12) Shirato, K.; Miyoshi, H.; Kariwa, H.; Takashima, I., J. Virol Methods 2005, 126, 119-125
(13) Prince, H. E.; Hogrefe, W. R., Clin. Appl. Immunol. Rev. 2005, 5, 45-63
(14) Gordon, S. M.; Isada, C. M. Cleveland Clin. J. Med. 2003, 70, 449-454
(15) Huang, C. N.; Slater, B.; Rudd, R.; Parchuri, N.; Hull, R.; Dupuis, M.; Hindenburg, A. Emerg. Infect. Dis. 2002, 8, 1367-1371
(16) Palmisano, F.; Malitesta, C.; Centonze, D.; Zambinin, P. G. Anal. Chem. 1995, 67, 2207-2211
(17) Wang, B.; Bouffier, L.; Demeunynck, M.; Mailley, P.; Roget, A.; Livache, T.; Dumy, P. Bioelectrochemistry 2004, 63, 233-237
(18) Korri-Youssoufi, H.; Makrouf, B. Anal. Chim. Acta 2002, 469, 85-92
(19) Cosnier, S.; Gondran, C.; Dueymes, C.; Simon, P.; Fontecave, M.; Decout, J. L. Chem. Soc., Chem. Commun. 2004, 1624-1625
(20) Hleli, S; Abdelghani, A; Tlili, A; Sensors, 3, 472-479
(21) Okahata Y.; Matsunobu, Y.; Ijiro, K.; Mukae, M.; Murakami, A.; Makino, K., J. Am. Chem. Soc. 1992, 114, 8299-8300

(22) Yongkang Ye; Huangxian Ju, Sensors, 2003, 3, 128-145
(23) Wang, J.; Rivas, G.; Fernandes, J. R.; Paz, J. L. L.; Jiang, M.; Waymire, R., Anal. Chim. Acta 1998, 375, 197-203
(24) Kambhampati, D.; Nielsen, P. E.; Knoll, W., Biosens. Bioelectron. 2001, 16, 1109
(25) Abel, A. P.; Weller, M. G.; Duveneck, G. L.; Ehrat, M.; Widmer, H. M., Anal. Chem. 1996, 68, 2905
(26) Ebersole, R. C.; Miller, J. A.; Moran, J. R.; Ward, M. D., J. Am. Chem. Soc. 1990, 112, 3239
(27) Symon, R. H.; Habili, N.; McInnes, J. L., J. Virol. Methods, 1989, 23, 299
(28) Guo Kejian, Scott Bowden, D., J. Clin. Microbiol. 1991, 29, 506-509
(29) Campbell, C. N.; Gal, D.; Critler, N.; Banditrat, C.; Heller, A., Anal. Chem. 2002, 74, 158-162
(30) de Lumley, T.; Campbell, C.; Heller, A., J. Am. Chem. Soc. 1996, 118, 5504
(31) Park, S. J.; Taton, T. A.; Mirkin, C. A., Science 2002, 295, 1503-1506
(43) Gottesfeld, J. M.; Melander, C.; Suto, R. K.; Raviol, H.; Luger, K.; Dervan, P. B., J. Mol. Biol. 2001, 309, 615-629
(44) Frank-Kamenetskii, M. D.; Mirkin, S. M., Annu. Rev. Biochem. 1995, 64, 65-95
(45) DiViacco, S.; Rapozzi, V.; Xodo, L.; Helene, C.; Quadrifoglio, F.; Giovannangeli, G., FASEB J. 2001, 15, 2660-2668
(46) Wang, J.; Rivas, G.; Cai, X., Electroanalysis 1997, 9, 395
(47) Armistead, P. M.; Thorp, H. H., Anal. Chem. 2000, 72, 3764-3770
(48) Arora, S. K., J. Am. Chem. Soc. 1983, 105, 1328-1332
(49) Makoto Takagi, Pure Appl. Chem. 2001, 73, 1573-1577
(50) Kelley, S. O.; Barton, J. K.; Jackson, N. M.; Hill, M. G., Bioconjugate Chem. 1997, 8, 31
(51) Hashimoto, K.; Ito, K.; Ishimori, Y.; Anal. Chem. 1994, 66, 3830
(52) Carter, M. T.; Rodriguez, M.; Bard, A. J., J. Am. Chem. Soc., 1989, 111, 8901

```
                              SEQUENCE LISTING

<160> NUMBER OF SEQ ID NOS: 2

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      WNV target DNA oligonucleotide

<400> SEQUENCE: 1
gctatttggc taccgtcagc atctctccac caaag                              35

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      WNV DNA biotin oligonucleotide

<400> SEQUENCE: 2
cggtagccaa atagc                                                    15
```

(32) Ihara, T.; Nakayama, M.; Murata, M.; Nakano, K.; Maeda, M., J. Chem. Soc. Chem. Commun. 1997, 1609
(33) Chun Xu, Hong Cai, Pingang He, Yuzhi Fang, Analyst 2001, 126, 62-65
(34) Palecek, E., Electroanalysis 1996, 8, 7
(35) Millan, K. M.; Mikkelsen, S. R., Anal. Chem. 1993, 65, 2317-2332
(36) Johnston, D. H.; Glasgow, K. C.; Thorp, H. H., J. Am. Chem. Soc. 1995, 117, 8933-8938
(37) Wong, E. L. S.; Gooding, J. J., Anal. Chem. 2003, 75, 3845-3852
(38) Takenaka, S.; Yamashita, K.; Takagi, M.; Uto, Y.; Kondo, H., Anal. Chem. 2000, 72, 1334-1341
(39) Dervan, P. B.; Burli, R. W., Curr. Opin. Chem. Biol. 1999, 3, 688-693
(40) Wemmer, D. E., Biopolymers 2001, 52, 197-211
(41) Pelton, J. G.; Werner, D. E., Proc. Natl. Acad. Sci. U.S.A. 1989, 36, 5723-5727
(42) Pelton, J. G.; Wemmer, D. E., Biochemistry, 1989, 27, 8088-8096

The invention claimed is:

1. A biosensor comprising a conductive or semi-conductive support and an intercalator polymer, wherein the intercalator polymer comprises monomer units of formula (I)

wherein:
P is an electropolymerizable moiety selected from the group consisting of pyrrole, acetylene, phenol, aniline, thiophene, carbazole and azulene;
Sp is a spacer; and
Im is an intercalator, and
wherein the molar ratio Im/P is between 1/10 and 1/5.

2. The biosensor of claim 1, comprising monomer units of the following formulas:

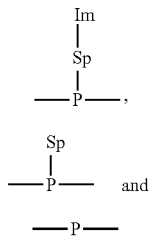

wherein P, Sp and Im are as defined in claim 1.

3. The biosensor of claim 1, wherein P is pyrrole.

4. The biosensor of claim 1, wherein the spacer Sp comprises an alkylenyl group, a cycloalkylenyl group, or an alkenylenyl group, whether or not substituted by one or more substituents.

5. The biosensor of claim 1, wherein the intercalator Im is selected from the group consisting of metal polypyridine complexes, organic dyes and compounds containing polycyclic aromatic rings.

6. The biosensor of claim 5, wherein the intercalator Im is a redox acridone derivative of formula (V)

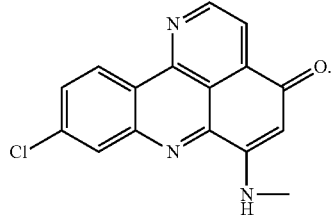

7. The biosensor of claim 1, wherein the intercalator polymer is coated on the conductive or semi-conductive support.

8. The biosensor of claim 1, wherein the conductive or semi-conductive support is selected from the group consisting of metallic supports and carbon materials.

9. The biosensor of claim 1, wherein the conductive or semi-conductive support is an electrode.

10. The biosensor of claim 9, wherein the conductive or semi-conductive support is an electrode and the electrode comprises a platinum disk with a diameter of about 0.5 cm.

11. A biosensor comprising a conductive or semi-conductive support and an intercalator polymer, wherein the intercalator polymer comprises monomer units of formula (I)

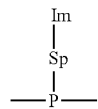

wherein:
P is an electropolymerizable moiety selected among the group consisting of pyrrole, acetylene, phenol, aniline, thiophene, carbazole and azulene;
Sp is a spacer, and
Im is an intercalator, and
wherein the intercalator Im is a redox acridone derivative of formula (V)

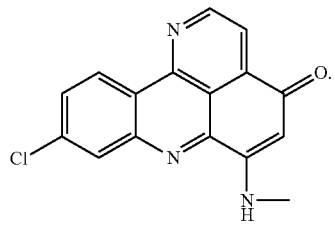

12. A biosensor comprising a conductive or semi-conductive support and an intercalator polymer, wherein the intercalator polymer comprises monomer units of formula (I)

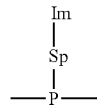

wherein:
P is an electropolymerizable moiety selected among the group consisting of pyrrole, acetylene, phenol, aniline, thiophene, carbazole and azulene;
Sp is a spacer, and
Im is an intercalator, and
wherein the conductive or semi-conductive support is an electrode and the electrode comprises in a platinum disk with a diameter of about 0.5 cm.

* * * * *